United States Patent
Matusz

(10) Patent No.: US 8,536,353 B2
(45) Date of Patent: Sep. 17, 2013

(54) PROCESS FOR THE PRODUCTION OF AN OLEFIN OXIDE, A 1,2-DIOL, A 1,2-DIOL ETHER, A 1,2-CARBONATE, OR AN ALKANOLAMINE

(75) Inventor: Marek Matusz, Houston, TX (US)

(73) Assignee: Shell Oil Company, Houston, TX (US)

(*) Notice: Subject to any disclaimer, the term of this patent is extended or adjusted under 35 U.S.C. 154(b) by 476 days.

(21) Appl. No.: 12/988,903

(22) PCT Filed: May 7, 2008

(86) PCT No.: PCT/US2008/062867
§ 371 (c)(1),
(2), (4) Date: Jan. 4, 2011

(87) PCT Pub. No.: WO2008/141030
PCT Pub. Date: Nov. 20, 2008

(65) Prior Publication Data
US 2011/0105771 A1 May 5, 2011

Related U.S. Application Data

(60) Provisional application No. 60/916,967, filed on May 9, 2007.

(51) Int. Cl.
*C07D 301/03* (2006.01)
*C07C 69/96* (2006.01)
*C07C 43/00* (2006.01)
*C07C 29/00* (2006.01)

(52) U.S. Cl.
USPC ............ 549/536; 558/260; 568/680; 568/867

(58) Field of Classification Search
USPC ................... 549/536; 558/260; 568/680, 867
See application file for complete search history.

(56) References Cited

U.S. PATENT DOCUMENTS

| | | | |
|---|---|---|---|
| 4,761,394 A | 8/1988 | Lauritzen | 502/348 |
| 4,766,105 A | 8/1988 | Lauritzen | 502/216 |
| 4,822,900 A | 4/1989 | Hayden | 549/534 |
| 4,845,296 A | 7/1989 | Ahmed et al. | 564/477 |
| 5,380,697 A | 1/1995 | Matusz et al. | 502/348 |
| 5,739,075 A | 4/1998 | Matusz | 502/302 |
| 5,801,259 A | 9/1998 | Kowaleski | 549/536 |
| 6,040,467 A | 3/2000 | Papavassiliou et al. | 549/534 |
| 6,368,998 B1 | 4/2002 | Lockemeyer | 502/347 |

FOREIGN PATENT DOCUMENTS

| | | |
|---|---|---|
| EP | 3642 | 8/1979 |
| WO | WO2004002954 | 1/2004 |
| WO | WO2004002971 | 1/2004 |
| WO | WO2004002972 | * 1/2004 |
| WO | WO2004/078737 | 9/2004 |
| WO | WO2004089539 | 10/2004 |
| WO | WO2006028940 | 3/2006 |
| WO | WO2006102189 | 9/2006 |
| WO | WO2007/095453 | 8/2007 |

OTHER PUBLICATIONS

Kirk-Othmer's Encyclopedia of Chemical Technology, $3^{rd}$ Edition, vol. 9, 1980. pp. 445-447.
Brunauer S, et al: Adsorption of Gases in Multimolecular Layers, Journal of the American Chemical Society, vol. 60 (1938), pp. 309-316.
PCT International Search Report dated Jul. 16, 2008 for Reference No. TH3225-PCT, Application No. PCT/US2008/062867 filed May 5, 2008.

* cited by examiner

*Primary Examiner* — Taylor Victor Oh

(57) ABSTRACT

A process for the epoxidation of an olefin comprising contacting a reactor feed comprising an olefin, oxygen, and carbon dioxide, with a catalyst comprising a carrier and, deposited on the carrier, silver, a rhenium promoter, a first co-promoter, and a second co-promoter; wherein the carbon dioxide is present in the reactor feed in a quantity of at most 3 mole percent based on the total epoxidation reactor feed; the first co-promoter is selected from sulfur, phosphorus, boron, and mixtures thereof; and the second co-promoter is selected from tungsten, molybdenum, chromium, and mixtures thereof; a process for preparing a 1,2-diol, a 1,2-diol ether, a 1,2-carbonate, or an alkanolamine.

19 Claims, No Drawings

PROCESS FOR THE PRODUCTION OF AN OLEFIN OXIDE, A 1,2-DIOL, A 1,2-DIOL ETHER, A 1,2-CARBONATE, OR AN ALKANOLAMINE

PRIORITY CLAIM

The present application claims priority to U.S. Provisional Patent Application 60/916,967 filed 9 May 2007.

FIELD OF THE INVENTION

The present invention relates to a process for the production of an olefin oxide, a 1,2-diol, a 1,2-diol ether, a 1,2-carbonate, or an alkanolamine.

BACKGROUND OF THE INVENTION

In olefin epoxidation, a reactor feed containing an olefin and oxygen is contacted with a catalyst under epoxidation conditions. The olefin is reacted with oxygen to form an olefin oxide. A product mix results that contains olefin oxide and, typically, unreacted reactor feed and combustion products.

Carbon dioxide is a by-product in the epoxidation process, and may be present in the reactor feed. Under commercial operation of epoxidation processes, the epoxidation reactor feed is formed by adding fresh oxygen and olefin to a recycle gas stream which comprises, besides unreacted and recycled oxygen and olefin, quantities of carbon dioxide, water, and other gases.

The olefin oxide may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine.

The catalytic epoxidation of olefins using a silver-based catalyst has been known for a long time. Conventional silver-based epoxidation catalysts have provided the olefin oxides notoriously in a low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximum selectivity of this reaction, based on the stoichiometry of the reaction equation $$7C_2H_4 + 6O_2 \Rightarrow 6C_2H_4O + 2CO_2 + 2H_2O,$$

cf. Kirk-Othmer's *Encyclopedia of Chemical Technology*, 3ed., vol. 9, 1980, p. 445.

Modern silver-based catalysts however are more selective towards olefin oxide production. When using the modern catalysts in the epoxidation of ethylene, the selectivity towards ethylene oxide can reach values above the 6/7 or 85.7 mole-% limit referred to. Such highly selective epoxidation catalysts are known from U.S. Pat. No. 4,766,105 and U.S. Pat. No. 4,761,394. However, the highly selective epoxidation catalysts employ higher reaction temperatures than do the conventional epoxidation catalysts for a given ethylene oxide yield, and they exhibit a greater rate of catalyst deactivation than conventional epoxidation catalysts.

The selectivity is the fraction of the converted olefin yielding the desired olefin oxide. As the catalyst ages, the fraction of the olefin converted normally decreases with time and to maintain a constant level of olefin oxide production the temperature of the reaction may be increased. However, this temperature increase adversely affects the selectivity of the conversion to the desired olefin oxide.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity over long periods yield substantial dividends in terms of process efficiency.

International Patent Application WO 2004/078737 discusses the improvement in performance of highly selective epoxidation catalysts during the production of ethylene oxide when the reactor feed contains less than 2 mole-% of carbon dioxide, relative to the total reactor feed.

It is desirable to find a way to further improve the epoxidation process, for example improving the selectivity of a highly selective epoxidation catalyst in the manufacture of olefin oxide while also improving the stability of such catalyst.

SUMMARY OF THE INVENTION

The present invention provides a process for the epoxidation of an olefin comprising contacting a reactor feed comprising an olefin, oxygen, and carbon dioxide, with a catalyst comprising a carrier and, deposited on the carrier, silver, a rhenium promoter, a first co-promoter, and a second co-promoter; wherein the carbon dioxide is present in the reactor feed in a quantity of at most 3 mole percent based on the total epoxidation reactor feed;

the first co-promoter is selected from sulfur, phosphorus, boron, and mixtures thereof; and the second co-promoter is selected from tungsten, molybdenum, chromium, and mixtures thereof.

The invention also provides a process for preparing a 1,2-diol, a 1,2-diol ether, a 1,2-carbonate, or an alkanolamine comprising obtaining an olefin oxide by the process for the epoxidation of an olefin according to the present invention, and converting the olefin oxide into the 1,2-diol, the 1,2-diol ether, the 1,2-carbonate, or the alkanolamine.

DETAILED DESCRIPTION OF THE INVENTION

In accordance with the invention, it has been found that a great improvement in the catalyst stability, in particular selectivity stability, as well as initial selectivity and other benefits can be obtained by contacting an olefin epoxidation reactor feed containing carbon dioxide in a quantity of at most 3 mole percent (mole-%), relative to the total reactor feed, with a highly selective epoxidation catalyst comprising silver, a rhenium promoter, a first co-promoter, and a second co-promoter.

Generally, the epoxidation catalyst is a supported catalyst. The carrier may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina.

The surface area of the carrier may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 20 m$^2$/g, preferably at most 10 m$^2$/g, more preferably at most 6 m$^2$/g, and in particular at most 4 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.3 to 0.6 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

The carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368, 998 and WO-A2-2007/095453, which are incorporated herein by reference. On the other hand, unwashed carriers may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

The preparation of the silver catalyst is known in the art and the known methods are applicable to the preparation of the catalyst which may be used in the practice of the present invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697, U.S. Pat. No. 5,739,075, U.S. Pat. No. 4,766,105, and U.S. Pat. No. 6,368,998, which are incorporated herein by reference. Suitably, silver dispersions, for example silver sols, may be used to deposit silver on the carrier. The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 190 g/kg, or 250 g/kg, or 350 g/kg. As used herein, unless otherwise specified, the weight of the catalyst is deemed to be the total weight of the catalyst including the weight of the carrier and catalytic components, for example silver, rhenium promoter, first and second co-promoters and further elements, if any.

The catalyst for use in the present invention additionally comprises a rhenium promoter component. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The rhenium promoter may be present in a quantity of at least 0.01 mmole/kg, preferably at least 0.1 mmole/kg, more preferably at least 0.5 mmole/kg, most preferably at least 1 mmole/kg, in particular at least 1.25 mmole/kg, more in particular at least 1.5 mmole/kg, calculated as the total quantity of the element relative to the weight of the catalyst. The rhenium promoter may be present in a quantity of at most 500 mmole/kg, preferably at most 50 mmole/kg, more preferably at most 10 mmole/kg, calculated as the total quantity of the element relative to the weight of the catalyst.

The catalyst for use in the present invention additionally comprises a first co-promoter component. The first co-promoter may be selected from sulfur, phosphorus, boron, and mixtures thereof. It is particularly preferred that the first co-promoter comprises, as an element, sulfur.

The catalyst for use in the present invention additionally comprises a second co-promoter component. The second co-promoter component may be selected from tungsten, molybdenum, chromium, and mixtures thereof. It is particularly preferred that the second co-promoter component comprises, as an element, tungsten and/or molybdenum, in particular tungsten. The form in which the first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

The first co-promoter may be present in a total quantity of at least 0.2 mmole/kg, preferably at least 0.3 mmole/kg, more preferably at least 0.5 mmole/kg, most preferably at least 1 mmole/kg, in particular at least 1.5 mmole/kg, more in particular at least 2 mmole/kg, calculated as the total quantity of the element (i.e., the total of sulfur, phosphorus, and/or boron) relative to the weight of the catalyst. The first co-promoter may be present in a total quantity of at most 50 mmole/kg, preferably at most 40 mmole/kg, more preferably at most 30 mmole/kg, most preferably at most 20 mmole/kg, in particular at most 10 mmole/kg, more in particular at most 6 mmole/ kg, calculated as the total quantity of the element relative to the weight of the catalyst.

The second co-promoter component may be present in a total quantity of at least 0.1 mmole/kg, preferably at least 0.15 mmole/kg, more preferably at least 0.2 mmole/kg, most preferably at least 0.25 mmole/kg, in particular at least 0.3 mmole/kg, more in particular at least 0.4 mmole/kg, calculated as the total quantity of the element (i.e., the total of tungsten, molybdenum, and/or chromium) relative to the weight of the catalyst. The second co-promoter may be present in a total quantity of at most 40 mmole/kg, preferably at most 20 mmole/kg, more preferably at most 10 mmole/kg, most preferably at most 5 mmole/kg, calculated as the total quantity of the element relative to the weight of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

In an embodiment, the catalyst comprises the rhenium promoter in a quantity of greater than 1 mmole/kg, relative to the weight of the catalyst, and the total quantity of the first co-promoter and the second co-promoter deposited on the carrier may be at most 3.8 mmole/kg, calculated as the total quantity of the elements (i.e., the total of sulfur, phosphorous, boron, tungsten, molybdenum and/or chromium) relative to the weight of the catalyst. In this embodiment, the total quantity of the first co-promoter and the second co-promoter may preferably be at most 3.5 mmole/kg, more preferably at most 3 mmole/kg of catalyst. In this embodiment, the total quantity of the first co-promoter and the second co-promoter may preferably be at least 0.1 mmole/kg, more preferably at least 0.5 mmole/kg, most preferably at least 1 mmole/kg of the catalyst.

The catalyst may preferably further comprise a further element deposited on the carrier. Eligible further elements may be one or more of nitrogen, fluorine, alkali metals, alkaline earth metals, titanium, hafnium, zirconium, vanadium, thallium, thorium, tantalum, niobium, gallium and germanium and mixtures thereof. Preferably, the alkali metals are selected from lithium, sodium, rubidium and cesium. Most preferably, the alkali metal is lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, calculated as the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may preferably further comprise a potassium promoter deposited on the carrier. The additional potassium promoter is preferred especially when the carrier utilized in making the catalyst contains low levels of leachable potassium. For example, the additional potassium promoter is especially preferred when the carrier contains nitric acid leachable potassium in a quantity of less than 85 ppmw, relative to the weight of the carrier, suitably at most 80 ppmw, more suitably at most 75 ppmw, most suitably at most 65 ppmw, same basis. The additional potassium promoter is especially preferred when the carrier contains water leachable potassium in a quantity of less than 40 ppmw, relative to the weight of the carrier, suitably at most 35 ppmw, more suitably at most 30 ppmw. In this embodiment, the potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with this embodiment can exhibit an improvement in selectivity, activity, and/or stability of the catalyst especially when operated under conditions where the reaction feed contains low levels of carbon dioxide, described hereinafter.

In an embodiment, the catalyst may preferably contain a quantity of potassium such that the amount of water extractable potassium of the catalyst may be at least 1.25 mmole/kg, relative to the weight of the catalyst, suitably at least 1.5 mmole/kg, more suitably at least 1.75 mmole/kg, same basis. Suitably, the catalyst may contain water extractable potassium in a quantity of at most 10 mmole/kg, more suitably at most 7.5 mmole/kg, most suitably at most 5 mmole/kg, same basis. Suitably, the catalyst may contain water extractable potassium in a quantity in the range of from 1.25 to 10 mmole/kg, more suitably from 1.5 to 7.5 mmole/kg, most suitably from 1.75 to 5 mmole/kg, same basis. The source of water extractable potassium may originate from the carrier and/or the catalytic components. The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which the reactor feed is contacted in the gas phase with the catalyst which is present as a solid material, typically in a packed bed. Generally the process is carried out as a continuous process.

The reactor feed of the inventive process comprises an olefin, oxygen and a quantity of carbon dioxide. The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the reactor feed may be selected within a wide range. Typically, the quantity of the olefin present in the reactor feed will be at most 80 mole percent, relative to the total reactor feed. Preferably, it will be in the range of from 0.5 to 70 mole percent, in particular from 1 to 60 mole percent, on the same basis. As used herein, the reactor feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole percent) or very high purity (at least 99.5 mole percent) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the reactor feed may be selected within a wide range. However, in practice, oxygen is generally applied in a quantity which avoids the flammable regime. Typically, the quantity of oxygen applied will be within the range of from 1 to 15 mole percent, more typically from 2 to 12 mole percent of the total reactor feed.

In order to remain outside the flammable regime, the quantity of oxygen present in the reactor feed may be lowered as the quantity of the olefin is increased. The actual safe operating ranges depend, along with the reactor feed composition, also on the reaction conditions such as the reaction temperature and the pressure.

An advantage of the present invention is that, when the epoxidation process is conducted in the presence of a catalyst containing silver, a rhenium promoter, a first co-promoter and a second co-promoter under process conditions such that the reactor feed contains low levels of carbon dioxide, an unexpected improvement in initial selectivity and selectivity stability can be observed. In an olefin oxide process a typical epoxidation reactor feed generally comprises a quantity of carbon dioxide exceeding 4 mole percent, relative to the total reactor feed. The process of the present invention is conducted under conditions where the quantity of carbon dioxide in the reactor feed is at most 3 mole percent, preferably less than 2.5 mole percent, more preferably less than 2 mole percent, most preferably less than 1.5 mole percent, in particular less than 1.2 mole percent, more in particular less than 1 mole percent, most in particular at most 0.75 mole percent, relative to the total reactor feed. In the normal practice of the present invention, the quantity of carbon dioxide present in the reactor feed is at least 0.1 mole percent, or at least 0.2 mole percent, or at least 0.3 mole percent, relative to the total reactor feed.

A reaction modifier may be present in the reactor feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the reactor feed, for example up to 0.1 mole percent, relative to the total reactor feed, for example from $0.01 \times 10^{-4}$ to 0.01 mole percent. In particular when the olefin is ethylene, it is preferred that the reaction modifier is present in the reactor feed in a quantity of from $0.1 \times 10^{-4}$ to $500 \times 10^{-4}$ mole percent, in particular from $0.2 \times 10^{-4}$ to $200 \times 10^{-4}$ mole percent, relative to the total reactor feed.

In addition to the olefin, oxygen and the reaction modifier, the reactor feed may contain one or more optional components, such as inert gases and saturated hydrocarbons. Inert gases, for example nitrogen or argon, may be present in the reactor feed in a quantity of from 30 to 90 mole percent, typically from 40 to 80 mole percent. Suitable saturated hydrocarbons are methane and ethane. If saturated hydrocarbons are present, they may be present in a quantity of up to 80 mole percent, relative to the total reactor feed, in particular up to 75 mole percent. Frequently, they are present in a quantity of at least 30 mole percent, more frequently at least 40 mole percent. Saturated hydrocarbons may be added to the reactor feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l·h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

The olefin oxide produced in the epoxidation process may be converted into a 1,2-diol, a 1,2-diol ether, a 1,2-carbonate, or an alkanolamine. As the present invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. The alkanolamine may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Preparation of Stock Silver Solution

This example describes the preparation of a stock silver impregnation solution used in preparing Catalyst A in Example 2.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh de-ionized water equal to the amount removed was added back to the silver solution. The solution was stirred for 15 minutes at 40° C. The process was repeated until the conductivity of the water removed was less than 90 μmho/cm. 1500 ml fresh de-ionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time. Water was removed from this mixture to leave a highly concentrated silver-containing slurry. The silver oxalate slurry was cooled to 30° C.

699 g of 92 weight percent ethylenediamine (8% de-ionized water) was added while maintaining a temperature no greater than 30° C. The final solution was used as a stock silver impregnation solution for preparing Catalyst A.

Example 2

Preparation of Catalysts

Catalyst A:

Catalyst A was prepared by the following procedure: To 296.7 grams of stock silver solution of specific gravity 1.545 g/ml was added 0.2723 g of ammonium perrhenate in 2 g of 1:1 ethylenediamine/water; 0.0759 g of ammonium metatungstate dissolved in 2 g of 1:1 ammonia/water; 0.1299 g of lithium sulfate monohydrate dissolved in 2 g of water; and 0.3194 g of lithium hydroxide monohydrate dissolved in water. Additional water was added to adjust the specific gravity of the solution to 1.528 g/ml. 100 g of the resulting solution was mixed with 0.2727 g of 50% w cesium hydroxide solution, producing the final impregnation solution. A vessel containing 30 grams of Carrier A hollow cylinders, see Table I below, was evacuated to 20 mm Hg for 1 minute and the final impregnation solution was added to Carrier A while under vacuum, then the vacuum was released and the carrier allowed to contact the liquid for 3 minutes. The impregnated Carrier A was then centrifuged at 500 rpm for 2 minutes to remove excess liquid. Impregnated Carrier A was placed in a vibrating shaker and dried in air flowing at a rate of 16.2 Nl/h at 250° C. for 7 minutes producing Catalyst A.

The final composition of Catalyst A comprised the following, calculated on the basis of pore volume impregnation: 17.2% w silver; 2 mmole Re/kg; 0.6 mmole W/kg; 2 mmole S/kg; 19 mmole Li/kg; and 5.6 mmole Cs/kg. These values are relative to the weight of the catalyst.

TABLE I

| Carrier A Properties | |
| --- | --- |
| Surface Area (m$^2$/g) | 0.75 |
| Water Absorption (%) | 47.2 |
| Packing Density (kg/m$^3$) | 837 |
| alpha alumina content (%) | 98.4 |
| Nitric Acid Leachable, ppmw: | |
| Na | 116 |
| K | 87 |
| Ca | 567 |
| Al | 607 |
| Mg | 81 |
| SiO$_2$ | 1474 |

Catalyst B:

Catalyst B was prepared in a similar manner as Catalyst A using Carrier B. The final composition of Catalyst B comprised the following, calculated on the basis of pore volume impregnation: 17.2% w silver; 2 mmole Re/kg; 0.6 mmole W/kg; 15 mmole Li/kg; and 3.8 mmole Cs/kg. These values are relative to the weight of the catalyst.

The cesium amounts of the above catalysts are the optimized cesium amounts with respect to the initial selectivity performance of the catalysts.

TABLE II

| Carrier B Properties | |
| --- | --- |
| Surface Area (m$^2$/g) | 0.73 |
| Water Absorption (%) | 49 |
| Packing Density (kg/m$^3$) | 811 |
| alpha alumina content (%) | 98.4 |

TABLE II-continued

| Carrier B Properties | |
| --- | --- |
| Nitric Acid Leachable, ppmw: | |
| Na | 121 |
| K | 86 |
| Ca | 549 |
| Al | 648 |
| Mg | 71 |
| SiO$_2$ | 1146 |

Example 3

Testing of Catalysts

The catalysts were used to produce ethylene oxide from ethylene and oxygen. To do this, 3 to 5 g of the crushed catalyst samples were loaded into stainless steel U-shaped tubes. Each tube was immersed in a molten metal bath (heat medium) and the ends were connected to a gas flow system. The weight of catalyst used and the inlet gas flow rate were adjusted to give a gas hourly space velocity of 3300 Nl/(l·h), as calculated for uncrushed catalyst. The inlet gas pressure was 1550 kPa (absolute).

Prior to startup, the catalysts were pre-treated for 3 hours with a gas mixture of 11.4 mole-% oxygen, 7 mole-% carbon dioxide and 81.6 mole-% nitrogen at 280° C. The reactor was then cooled down to 240° C. and a testing gas mixture was introduced. The initial gas mixture passed through the catalyst bed in a "once-through" operation and consisted of 30 volume percent ethylene, 8 volume percent oxygen, 5 volume percent carbon dioxide, 57 volume percent nitrogen and 1.0 to 4.0 parts per million by volume (ppmv) ethyl chloride. During the testing of the catalyst, the temperature was adjusted so as to achieve a constant ethylene oxide content of 3.09 volume percent in the outlet gas stream. The quantity of ethyl chloride was varied to obtain maximum selectivity. Catalyst A was additionally subjected to conditions where the ethyl chloride was decreased to zero for 24 hours during which time the temperature was changed to 260° C. For Catalyst A, the initial gas mixture was used for the first 10 days of the test run. For Catalyst B, the initial gas mixture was used for the first 18 days of the test run. After this initial testing period, the gas mixture was changed to comprise 30 volume percent ethylene, 8 volume percent oxygen, 1 volume percent carbon dioxide, 61 volume percent nitrogen and 1.0 to 4.0 parts per million by volume (ppmv) ethyl chloride, which was maintained for the remainder of the test run.

During the testing of the catalyst, the temperature was adjusted so as to achieve a constant ethylene oxide content of 3.09 volume percent in the outlet gas stream. The quantity of ethyl chloride was varied to obtain maximum selectivity. Initial performance data at this productivity level was measured between 2 to 3 weeks of operation, once the process equilibrated after the quantity of carbon dioxide in the gas mixture was lowered to 1 mole-%, relative to the total gas mixture. Additional selectivity and temperature values were measured over time in order to obtain catalyst stability data.

As observed from the data in Table III, the epoxidation process using Catalyst A, according to the present invention, exhibits an unexpected improvement in initial selectivity and selectivity stability at the same ethylene oxide production levels, as compared to the comparative epoxidation process using Catalyst B.

TABLE III

| Catalyst | Initial Selectivity (%) | Initial Temperature (° C.) | Selectivity (%) Run Time = 86 days [Δ % S] | Temperature (° C.) Run Time = 86 days [Δ ° C.] | Selectivity (%) Run Time = 229 days [Δ % S] | Temperature (° C.) Run Time = 229 days [Δ ° C.] | Selectivity (%) Run Time = 386 days [Δ % S] | Temperature (° C.) Run Time = 386 days [Δ ° C.] |
|---|---|---|---|---|---|---|---|---|
| A*) | 91 | 245 | 91 [0] | 252 [7] | 89 [−2] | 262 [17] | 88.4 [−2.6] | 266 [21] |
| B**) | 89.7 | 245 | 88.8 [−0.9] | 250 [5] | 87.2 [−2.5] | 256 [11] | *** | *** |

*)process according to the invention
**)comparative process
***data unavailable

Example 4

Catalyst C was prepared using Carrier C and having a final composition of the following, calculated on the basis of pore volume impregnation: 17.5% w silver; 2 mmole Re/kg; 0.6 mmole W/kg; 2 mmole S/kg; 19 mmole Li/kg; 2 mmole K/kg; and 3.8 mmole Cs/kg. These values are relative to the weight of the catalyst. Ammonium perrhenate, ammonium metatungstate, ammonium sulfate, lithium hydroxide, potassium nitrate and cesium hydroxide were used to prepare Catalyst C.

TABLE IV

| Carrier C Properties | |
|---|---|
| Surface Area (m²/g) | 0.73 |
| Water Absorption (%) | 47.8 |
| Packing Density (kg/m³) | 838 |
| alpha alumina content (%) | 98.4 |
| Nitric Acid Leachable, ppmw: | |
| Na | 131 |
| K | 83 |
| Ca | 533 |
| Al | 655 |
| Mg | 74 |
| SiO₂ | 1456 |

A tubular pilot reactor was charged with 12.24 kg of whole catalyst pellets in the form of a hollow cylinder having a nominal outer diameter of 8 mm, a nominal inner diameter of 1 mm and a nominal length of 8 mm. The coolant (water) surrounding the tubular reactor was heated from 40 to 220° C. over 17 hours and a flow of $N_2$ gas at GHSV of 1100 Nl/l/h was introduced into the reactor tube. Once the coolant temperature reached 220° C., ethylene was added to the reactor feed gas and brought to 25 vol %. After the desired ethylene concentration was achieved, air was introduced in the reactor feed to initiate reaction of ethylene and oxygen to ethylene oxide. At essentially the same time as air was introduced to the reactor, ethyl chloride was introduced and brought to a concentration of 2-2.5 ppmv. During the next 6 hours of operation, the air feed rate was increased until an oxygen concentration of 4.0 vol % was achieved at the reactor inlet. As the oxygen was increased, the coolant temperature was increased to 235° C., carbon dioxide was introduced and brought to 0.8 vol %, and the total flow was increased to a GHSV of 3320 Nl/l/h. The inlet pressure to the reactor was maintained at 241 psig throughout the experiment. A total of 0.15 grams of ethyl chloride per kilogram of catalyst was introduced. For the next 17 hours, ethyl chloride was reduced to 1.4 ppmv and all other conditions were held constant at GHSV of 3320 Nl/l/h, 235° C. coolant temperature, 241 psig inlet pressure, and ethylene/oxygen/carbon dioxide composition of 25:4:0.8. During the next 7 hours, ethylene was increased from 25 to 35 vol %, oxygen was increased from 4.0 to 7.5 vol %, and ethyl chloride was increased from 1.4 ppmv to 1.91 ppmv. All other gas flows and compositions were held constant. At the end of this step, the coolant temperature was adjusted to 227° C. to achieve an ethylene oxide concentration of 2.7 vol % in the outlet of the reactor. During the following 24 hours, the ethyl chloride concentration was increased to 2.05 ppmv to obtain the optimal catalyst selectivity. At the end of the start-up process (i.e., during step 6), the selectivity was 90.3% at a temperature of 228° C. Details of the changing reactor conditions are set out in Table V.

TABLE V

| Step | Temperature, ° C. | GHSV, Nl/l/h | O₂, % | C₂H₄, % | CO₂, % | Ethyl Chloride, ppmv | Time, h |
|---|---|---|---|---|---|---|---|
| 1 | 40 to 220 | 1100 | 0 | 0 | 0 | 0 | 17 |
| 2 | 220 | 1100 | 0 | 25 | 0 | 0 | 1 |
| 3 | 220 to 235 | 1100 to 3320 | 0 to 4 | 25 | 0-0.8 | 2 to 2.5 | 6 |
| 4 | 235 | 3320 | 4 | 25 | 0.8 | 1.4 | 17 |
| 5 | 235 to 227 | 3320 | 4 to 7.5 | 25 to 35 | 0.8 | 1.4 to 1.91 | 7 |
| 6 | 228 | 3320 | 7.5 | 35 | 0.8 | 2.05 | 24 |

During the start-up process and initial epoxidation production, the quantity of ethylene may be maintained at a constant level and different amounts may be utilized, for example the quantity of ethylene may be 25 mole-%, 35 mole-%, or 40 mole-%. The quantity of oxygen may be varied within flammability limits. The length of step 4 may be varied from 1 to 30 hours, shorter periods of time may be preferred for higher production levels.

What is claimed is:

1. A process for the epoxidation of an olefin comprising:
contacting a reactor feed comprising an olefin, oxygen, and carbon dioxide, with a catalyst comprising a carrier and, deposited on the carrier, silver, a rhenium promoter, a first co-promoter, and a second co-promoter; wherein
the carbon dioxide is present in the reactor feed in a quantity of at most 3 mole percent based on the total reactor feed;
the first co-promoter is selected from the group consisting of sulfur, phosphorus, boron, and mixtures thereof; and
the second co-promoter is selected from the group consisting of tungsten, molybdenum, chromium, and mixtures thereof.

2. The process as claimed in claim 1, wherein the quantity of carbon dioxide is less than 2 mole percent based on the total reactor feed.

3. The process as claimed in claim 1, wherein the quantity of carbon dioxide is in the range of from 0.2 to less than 1.5 mole percent based on the total reactor feed.

4. The process as claimed in claim 1, wherein the olefin is ethylene.

5. The process as claimed in claim 1, wherein the second co-promoter comprises tungsten.

6. The process as claimed in claim 1, wherein the second co-promoter comprises molybdenum.

7. The process as claimed in claim 1, wherein the first co-promoter comprises sulfur.

8. The process as claimed in claim 1, wherein the catalyst further comprises a further element selected from the group consisting of nitrogen, fluorine, alkali metals, alkaline earth metals, titanium, hafnium, zirconium, vanadium, thallium, thorium, tantalum, niobium, gallium, germanium, and mixtures thereof.

9. The process as claimed in claim 1, wherein the catalyst has a water extractable quantity of potassium in the range of from 1.25 to 10 mmole/kg, relative to the weight of the catalyst.

10. The process as claimed in claim 1, wherein the catalyst further comprises deposited on the carrier a potassium promoter in a quantity of at least 0.5 mmole/kg, relative to the weight of the catalyst.

11. The process as claimed in claim 1, wherein the rhenium promoter is present in a quantity in the range of from 0.1 to 50 mmole/kg, relative to the weight of the catalyst.

12. The process as claimed in claim 1, wherein the molar ratio of the rhenium promoter to the second co-promoter is greater than 1.

13. The process as claimed in claim 1, wherein the first co-promoter is present in a quantity in the range of from 0.2 to 50 mmole/kg, relative to the weight of the catalyst and the second co-promoter is present in a quantity in the range of from 0.1 to 40 mmole/kg, relative to the weight of the catalyst.

14. The process as claimed in claim 1, wherein the molar ratio of the first co-promoter to the second co-promoter is greater than 1.

15. A process for preparing a 1,2-diol, a 1,2-diol ether, a 1,2-carbonate, or an alkanolamine comprising:

contacting a reactor feed comprising an olefin, oxygen, and carbon dioxide, with a catalyst so as to form an olefin oxide, wherein the catalyst comprises a carrier and, deposited on the carrier, silver, a rhenium promoter, a first co-promoter, and a second co-promoter, wherein the carbon dioxide is present in the reactor feed in a quantity of at most 3 mole percent based on the total reactor feed;

wherein the first co-promoter is selected from the group consisting of sulfur, phosphorus, boron, and mixtures thereof; and wherein the second co-promoter is selected from the group consisting of tungsten, molybdenum, chromium, and mixtures thereof; and converting the olefin oxide into the 1,2-diol, the 1,2-diol ether, the 1,2-carbonate, or the alkanolamine.

16. The process as claimed in claim 15, wherein the first co-promoter is sulfur and the second co-promoter is tungsten.

17. The process as claimed in claim 16, wherein the molar ratio of the first co-promoter to the second co-promoter is in the range of from greater than 1 to 20.

18. The process as claimed in claim 1, wherein the first co-promoter is sulfur and the second co-promoter is tungsten.

19. The process as claimed in claim 18, wherein the molar ratio of the first co-promoter to the second co-promoter is in the range of from greater than 1 to 20.

* * * * *